United States Patent [19]

Khandare et al.

[11] Patent Number: 5,773,673
[45] Date of Patent: Jun. 30, 1998

[54] METHOD OF MAKING CHLORINATED HYDROCARBONS

[75] Inventors: Pravin M. Khandare, Amherst; Edward A. Rowe, Grand Island, both of N.Y.

[73] Assignee: Occidental Chemical Corporation, Niagara Falls, N.Y.

[21] Appl. No.: 886,427

[22] Filed: Jul. 1, 1997

[51] Int. Cl.$^6$ .................................................. C07C 17/10
[52] U.S. Cl. ..................... 570/252; 570/246; 204/157.95
[58] Field of Search ....................... 204/157.95; 570/246, 570/252

[56] References Cited

U.S. PATENT DOCUMENTS

| | | | |
|---|---|---|---|
| 3,070,636 | 12/1962 | Kieras | 570/262 |
| 3,349,008 | 10/1967 | Vives | 570/262 |
| 3,541,164 | 11/1970 | Washall | 570/262 |
| 3,544,641 | 12/1970 | Versnel | 570/262 |
| 3,560,373 | 2/1971 | Washall | 570/262 |
| 5,495,058 | 2/1996 | Stevenson et al. | |

FOREIGN PATENT DOCUMENTS

0401924 A  12/1990  European Pat. Off. ............... 570/262

*Primary Examiner*—Alan Siegel
*Attorney, Agent, or Firm*—Richard D. Fuerle

[57] ABSTRACT

Disclosed is a method of making chlorinated hydrocarbons. A mixture is prepared of a hydrocarbon or partially chlorinated hydrocarbon from $C_{18}$ to $C_{30}$ and either benzotrifluoride or parachlorobenzotrifluoride in an amount sufficient to liquefy the mixture at the chlorination temperature. The mixture is heated to a temperature of about 50° to 100° C. and sufficient chlorine gas is passed therethrough in the presence of UV light to form a chlorinated hydrocarbon that is about 60 to about 80 wt. % chlorine. One part by weight of the composition is added to at least two parts by weight per part of a $C_1$ to $C_6$ monohydric alcohol, which results in the precipitation of the chlorinated hydrocarbon. The precipitated chlorinated hydrocarbon can be removed from the composition by, for example, filtration.

20 Claims, No Drawings

METHOD OF MAKING CHLORINATED HYDROCARBONS

BACKGROUND OF THE INVENTION

Disclosed is a method of making a chlorinated hydrocarbon by contacting a mixture of a hydrocarbon in benzotrifluoride or parachlorobenzotrifluoride with chlorine gas. In particular, it relates to the improvement wherein the chlorinated hydrocarbon is precipitated from the mixture by the addition of a monohydric alcohol.

Chlorinated hydrocarbons have been made by sparging gaseous chlorine into a solution of a hydrocarbon in carbon tetrachloride. The solution was heated to strip the carbon tetrachloride off the chlorinated hydrocarbon. When it was discovered that carbon tetrachloride was a carcinogen and an ozone depleter, it was replaced by other solvents such as benzotrifluoride (BTF) and parachlorobenzotrifluoride (PCBTF), as is described in U.S. Pat. No. 5,495,058, herein incorporated by reference. According to that patent, chlorinated paraffins can be made by chlorinating paraffins in solvents such as BTF and PCBTF, which are then distilled from the solution to obtain a molten chlorinated wax. However, because chlorinated hydrocarbons tend to decompose at the temperatures required for this distillation, the product may be discolored, which is regarded as undesirable by customers.

SUMMARY OF THE INVENTION

We have discovered an improved process for making chlorinated hydrocarbons using BTF or PCBTF as a solvent. In the process of this invention, the solvent is not distilled from the chlorinated hydrocarbon, but rather the solution of the chlorinated hydrocarbon in the solvent is added to an alcohol which results in the precipitation of the chlorinated hydrocarbon. It is then collected and separated from the solvent.

Since the chlorinated hydrocarbon is not heated during distillation in the method of this invention, energy is saved and the products are not discolored and are more acceptable to customers.

DESCRIPTION OF THE PREFERRED EMBODIMENTS

This invention is applicable to aliphatic hydrocarbons (open chain compounds of only hydrogen and carbon) containing 18 to 30 carbon atoms. Such hydrocarbons may be saturated (i.e., paraffins) or unsaturated (i.e., olefins). The olefins may have one or two double bonds but are preferably single bonded alpha olefins. Linear hydrocarbons are preferred because they are commercially in demand and there are fewer applications for chlorinated branched hydrocarbons. For paraffins, hydrocarbons of 20 to 28 carbon atoms are preferred and, for olefins, hydrocarbons of 24 to 28 carbons atoms are preferred as those hydrocarbons are economical and commercially available.

The hydrocarbons can initially be partially chlorinated in a solvent or the solvent can be omitted because the resulting partially chlorinated hydrocarbon is a liquid. Either BTF or PCBTF can be used as a solvent; PCBTF is preferred because it is less flammable and is exempt from many government regulations that relate to toxicity and ozone depletion.

Once the hydrocarbon has been partially chlorinated, sufficient solvent is used to facilitate heat transfer and mixing and form a liquid mixture of the solvent and the chlorinated hydrocarbon at the temperature of chlorination. It is preferable that the liquid mixture have a viscosity below about 50 MPa·s so that it can be easily mixed and sparged with chlorine gas. Excess solvent should be avoided, however, as it is unnecessary and uneconomical. Generally, the solvent should be less than about 75 wt. % of the mixture weight. All of the solvent can be initially mixed with the hydrocarbon or some of the solvent can be used initially and the remainder added later. This latter procedure is used when a portion of the hydrocarbon is partially chlorinated and sold as a solution in the solvent, then the remaining hydrocarbon is further chlorinated, because additional solvent is required to solubilize the more viscous, more highly chlorinated hydrocarbon.

Chlorination can be performed at about 50° to about 100° C., but is preferably performed at about 60° to about 80° C. as the reaction is slower at lower temperatures and higher temperatures may degrade the hydrocarbon. Gaseous chlorine is sparged through the solution to effect the chlorination. The amount of chlorine used corresponds to the stoichiometric amount required to achieve the desired amount of chlorination. Chlorine free radicals (Cl·) are generated using an initiator such as UV light or an alkane nitrile. The chlorination reaction may take about 8 hours and is complete when all of the allotted chlorine has reacted.

As a general rule, olefins chlorinate across the double bond first and then the chlorine adds to alternating carbon atoms, and paraffins chlorinate in the 2 position first then alternating carbon atoms. The product will be about 60 to about 80 wt. % chlorine. If the product contains less chlorine, a solvent is unnecessary and this invention is not applicable; it is usually uneconomical to chlorinate the product to more than 80 wt. % chlorine. Preferably, the product contains about 70 to 80 wt. % chlorine.

Once the chlorination is complete, the solution can be cooled to room temperature. Unreacted chlorine and dissolved hydrogen chloride can be removed by sparging with nitrogen under vacuum.

In the next step, the chlorinated hydrocarbon is precipitated from the solution. This is accomplished by adding the solution to at least two times as much (by weight) of a $C_1$ to $C_6$ monohydric alcohol. Preferably, $C_1$ to $C_4$ monohydric alcohols are used as higher alcohols have an undesirable odor and offer no additional benefit and their higher boiling points may make them difficult to separate from the solvent. Particularly preferred are methanol, ethanol, and isopropanol, because n-butanol, isobutanol, and n-propanol form azeotropes with benzotrifluoride and parachlorobenzotrifluoride which makes them difficult to separate; methanol is especially preferred because the vapor pressure difference between methanol and PCBTF is large, which facilitates separation of methanol and PCBTF by distillation. To avoid having to evaporate alcohol, no more alcohol should be used than is necessary, and two to three times the weight of the solution is usually adequate.

The precipitated chlorinated hydrocarbon can be separated from the solvent by a variety of techniques, such as filtration or centrifugation. The remaining liquid, a mixture of the solvent and the alcohol, is distilled to separate the solvent from the alcohol. The separated solvent and alcohol can be recycled and reused. The precipitated chlorinated hydrocarbon can be dried and crushed if desired. It can be used as a fire retardant for rubber compounding and as an additive for film forming polymers to reduce their cost. It can also be used in coatings and paints.

The following examples further illustrate this invention.

EXAMPLE 1

A reactor was charged with 77.12 g of $C_{24}$ paraffin and 231.47 g PCBTF. The mixture was heated to 85° C. and chlorine gas was sparged into it. Due to the reaction exotherm, the temperature reached 91° to 92° C. After the desired amount of chlorine (135.6 g) had been sparged in, the reaction was stopped and the product was purged with nitrogen to remove unreacted chlorine and HCl from the reaction mass. The reaction product, 362.44 g, was discharged into a bottle. A portion of the reaction mass was subject to the alcohol separation technique and yielded a chlorinated wax containing 46.2 wt. % chlorine.

EXAMPLE 2

Example 1 was repeated using 75.61 g of $C_{20}$ to $C_{24}$ alpha olefin, 222.98 g of PCBTF, and 124.92 g chlorine. The reaction temperature was 89° to 90° C. and 373.2 g of product having a chlorine content of 50.2 wt. % was recovered.

EXAMPLE 3

Preparation of highly chlorinated paraffin (~80 wt. % due to chlorine) from partially chlorinated paraffin (50 wt. % due to chlorine)

Partially chlorinated (about 50 wt. %) paraffin sold by Occidental Chemical Corporation as "Chlorowax 50" or "CWX 50" was dissolved in a 1:3 weight ratio in PCBTF sold by Occidental Chemical Corporation as "Oxsol 100." The resulting mixture, which was white in color with a yellow tint, was chlorinated using UV light and chlorine gas. The reaction was maintained between 55° and 90° C.; HCl off gas was collected in a scrubber. After the reaction was complete, the mixture was siphoned out warm into a glass sample bottle. Chlorine and hydrogen chloride balance during the chlorination reaction helped to ascertain the chlorination endpoint.

EXAMPLE 4

In a lab preparation, 2 g of the product mixture of Example 3, chlorinated paraffin in PCBTF, was poured into a beaker to which 6 g of methanol had been added. A milky white precipitate formed almost instantaneously. The liquid phase was decanted from the beaker and the product was dried by blowing warm nitrogen over it. The procedure was repeated using 6 g of ethanol and a similar result occurred.

EXAMPLE 5

Approximately 10 g of the product mixture of Example 3 was mixed with 30 g of ethanol. A white precipitate formed immediately. It was separated from the liquid phase by decantation. The chlorinated paraffin product was dried in an oven with a nitrogen purge for 30 min. The dried solid product was off-white in color and was 66 wt. % chlorine.

EXAMPLE 6

Preparation of highly chlorinated alpha olefin (~70 wt. % due to chlorine) from partially chlorinated alpha olefin (50 wt. % due to chlorine)

To 62.3 g of ethanol was added 24.04 g of 50 wt. % chlorinated $C_{24}$ to $C_{28}$ olefin in PCBTF, resulting in the instantaneous formation of a white precipitate. The precipitate was separated from the liquid by decantation. Warm nitrogen was blown over the precipitate in a Petri dish. The resulting chlorinated olefin was analyzed to contain approximately 50 wt. % chlorine.

The viscosity of the product (in MPa·s) was determined to be 13200 at 25.3° C., 1250 at 50.6° C., and 260 at 75.4° C. The viscosity of a mixture of 25 wt. % of the product and 75 wt. % PCBTF was determined to be 5 at 25.4° C.

EXAMPLE 7

The 50 wt. % chlorinated $C_{24}$ to $C_{28}$ olefin starting material used in Example 3 was further chlorinated by sparging chlorine gas into it at about 50° C. in the presence of UV light. To 59.62 g of ethanol was added 19.67 g of the chlorinated olefin in PCBTF, resulting in the formation of a white precipitate. The liquid was separated by decantation and warm nitrogen was blown over the sample in a Petri dish. The resulting chlorinated olefin was found to contain approximately 70 wt. % chlorine. A mixture was prepared of 30 wt. % of this product and 70 wt. % PCBTF. The viscosity of the mixture (in MPa·s) was 65 at 25.3° C. and 15 at 50.3° C.

EXAMPLE 8

To 120.62 g of ethanol was added 102.18 g of a reaction mixture of 70 wt. % chlorinated $C_{20}$ to $C_{24}$ alpha olefin and PCBTF in a 1:3 weight ratio. A milky white precipitate weighing approximately 28 g formed and was separated by decantation. The precipitate was warmed by passing a nitrogen purge over it, which removed trace amounts of solvents (ethanol and PCBTF) from it. An analysis showed that the precipitate was 80 wt. % chlorine.

We claim:

1. A method of making chlorinated hydrocarbons comprising
   (A) preparing a mixture which comprises
      (1) hydrocarbon or partially chlorinated hydrocarbon from $C_{18}$ to $C_{30}$; and
      (2) a solvent selected from the group consisting of benzotrifluoride and parachlorobenzotrifluoride in an amount sufficient to liquefy said mixture, at a temperature of about 50° to about 100° C.;
   (B) heating said mixture to a temperature of about 50° to about 100° C.;
   (C) adding chlorine gas to said mixture in an amount sufficient to produce a composition containing a chlorinated hydrocarbon that is about 60 to about 80 wt. % chlorine;
   (D) converting said chlorine into chlorine free radicals;
   (E) adding said composition to at least two parts by weight of a $C_1$ to $C_6$ monohydric alcohol per part by weight of said composition, whereby said chlorinated hydrocarbon precipitates; and
   (F) collecting said precipitated chlorinated hydrocarbon.

2. A method according to claim 1 wherein said solvent is parachlorobenzotrifluoride.

3. A method according to claim 1 wherein said hydrocarbon is a linear paraffin.

4. A method according to claim 3 wherein said paraffin has 20 to 26 carbon atoms.

5. A method according to claim 1 wherein said hydrocarbon is a linear α-olefin that has a single double bond.

6. A method according to claim 5 wherein said olefin has 24 to 28 carbon atoms.

7. A method according to claim 1 wherein said chlorinated hydrocarbon is about 70 to about 80 wt. % chlorine.

8. A method according to claim 1 wherein, between steps (C) and (D), said composition is cooled to room temperature, and hydrogen chloride and unreacted chlorine are removed.

9. A method according to claim 1 wherein said alcohol is methanol, ethanol, or isopropanol.

10. A method according to claim 1 including the additional last steps of distilling remaining composition to separate said solvent from said $C_1$ to $C_6$ monohydric alcohol and recycling said solvent to step (A) and said alcohol to step (E).

11. In a process for chlorinating hydrocarbons by dissolving a $C_{18}$ to $C_{30}$ hydrocarbon or partially chlorinated hydrocarbon in a solvent to form a solution, heating said solution, and sparging chlorine gas therethrough in the presence of ultraviolet light to produce chlorinated hydrocarbons, an improved method of separating said chlorinated hydrocarbons from said solution comprising adding said solution to at least twice its weight of a $C_1$ to $C_6$ monohydric alcohol, thereby precipitating said chlorinated hydrocarbons, and collecting said precipitated chlorinated hydrocarbons therefrom.

12. A process according to claim 11 wherein said alcohol is methanol.

13. A process according to claim 11 wherein said alcohol is ethanol.

14. A process according to claim 11 wherein said alcohol is isopropanol.

15. A process according to claim 11 wherein said hydrocarbon is a $C_{20}$ to $C_{28}$ linear paraffin.

16. A process according to claim 11 wherein said hydrocarbon is a linear α-olefin that has a single double bond.

17. A method of making chlorinated paraffins comprising
   (A) preparing a mixture which comprises
      (1) $C_{20}$ to $C_{28}$ paraffins; and
      (2) parachlorobenzotrifluoride in an amount sufficient to form a solution of said mixture at a temperature of about 60° to about 80° C.;
   (B) heating said mixture to a temperature between about 60° and about 80° C. to form said solution;
   (C) adding chlorine gas to said solution in an amount sufficient to produce a composition containing a chlorinated paraffin that is about 70 to about 80 wt. % chlorine;
   (D) exposing said solution to UV light;
   (E) cooling said solution to room temperature;
   (F) removing unreacted chlorine gas and dissolved hydrogen chloride from said solution;
   (G) adding said solution to about 2 to about 3 parts by weight per part by weight of said solution of an alcohol selected from the group consisting of methanol, ethanol, and isopropanol, whereby said chlorinated paraffin precipitates;
   (H) separating said precipitated chlorinated paraffin from said solution;
   (I) distilling said solution to separate said parachlorobenzotrifluoride from said alcohol;
   (J) recycling said parachlorobenzotrifluoride to step (A); and
   (K) recycling said alcohol to step (G).

18. A method according to claim 17 wherein said precipitated chlorinated paraffin is separated from said solution by filtration.

19. A method according to claim 17 wherein said unreacted chlorine gas and dissolved hydrogen chloride are removed by sparging with nitrogen.

20. A method according to claim 17 wherein said alcohol is methanol.

* * * * *